United States Patent
Wei et al.

(10) Patent No.: US 12,060,584 B2
(45) Date of Patent: Aug. 13, 2024

(54) D-AMINO ACID OXIDASE MUTANTS AND USES THEREOF IN PREPARING L-GLUFOSINATE

(71) Applicants: YONGNONG BIOSCIENCES CO., LTD., Zhejiang (CN); EAST CHINA UNIVERSITY OF SCIENCE AND TECHNOLOGY, Shanghai (CN); NINGXIA YONGNONG BIOSCIENCES CO., LTD., Ningxia (CN)

(72) Inventors: Dongzhi Wei, Shanghai (CN); Hualei Wang, Shanghai (CN); Chengjun Wu, Shaoxing (CN); Qinghai Liu, Shanghai (CN); Jian Zhang, Shanghai (CN); Zhonghua Luo, Yinchuan (CN); Changlei Zhang, Shaoxing (CN)

(73) Assignees: YONGNONG BIOSCIENCES CO, LTD, Shaoxing (CN); EAST CHINA UNIVERSITY OF SCIENCE AND TECHNOLOGY, Shanghai (CN); NINGXIA YONGNONG BIOSCIENCES CO., LTD., Yinchuan (CN)

( * ) Notice: Subject to any disclaimer, the term of this patent is extended or adjusted under 35 U.S.C. 154(b) by 0 days.

(21) Appl. No.: 18/469,527

(22) Filed: Sep. 18, 2023

(65) Prior Publication Data
US 2024/0101974 A1 Mar. 28, 2024

Related U.S. Application Data

(63) Continuation of application No. PCT/CN2022/089830, filed on Apr. 28, 2022.

(30) Foreign Application Priority Data

Apr. 29, 2021 (CN) .......................... 202110475247.9

(51) Int. Cl.
C12N 9/06 (2006.01)
C12N 9/08 (2006.01)
C12N 15/70 (2006.01)
C12P 13/04 (2006.01)

(52) U.S. Cl.
CPC ......... *C12N 9/0024* (2013.01); *C12N 9/0065* (2013.01); *C12N 15/70* (2013.01); *C12P 13/04* (2013.01); *C12Y 104/01005* (2013.01); *C12Y 111/01006* (2013.01)

(58) Field of Classification Search
CPC .... C12N 9/0024; C12N 9/0065; C12N 15/70; C12P 13/04; C12Y 104/01005; C12Y 111/01006; C12Y 104/03003
See application file for complete search history.

(56) References Cited

U.S. PATENT DOCUMENTS 5,587,319 A 12/1996 Then et al.
2008/0153137 A1 6/2008 Archer et al.

FOREIGN PATENT DOCUMENTS

| | | | |
|---|---|---|---|
| CN | 1714146 | A | 12/2005 |
| CN | 1922328 | A | 2/2007 |
| CN | 101194020 | A | 6/2008 |
| CN | 109609477 | A | 4/2019 |
| CN | 106916857 | B | 8/2019 |
| CN | 106978453 | B | 10/2019 |
| CN | 109750009 | B | 12/2019 |
| CN | 111139270 | A | 5/2020 |
| CN | 110343676 | B | 6/2020 |
| CN | 111321193 | A | 6/2020 |
| CN | 109609475 | B | 10/2020 |
| CN | 107502647 | B | 12/2020 |
| CN | 110791484 | B | 12/2020 |
| CN | 112626142 | A | 4/2021 |
| CN | 111019982 | B | 10/2021 |
| CN | 113969268 | A | 1/2022 |
| CN | 113969269 | A | 1/2022 |
| WO | 2006061137 | A1 | 6/2006 |
| WO | 2009099728 | A1 | 8/2009 |
| WO | 2015181119 | A2 | 12/2015 |
| WO | 2017151573 | A1 | 9/2017 |

OTHER PUBLICATIONS

GenBank Accession No. SCV69635.1, BQ2448_2655 [*Microbotryum intermedium*], GenBank Database, 2017, 2 pages.
Cao, Cheng-Hao et al., Enzyme Cascade for Biocatalytic Deracemization of D, L-phosphinothricin, Journal of Biotechnology, 1-8, 2020.
Chen, Guoqiang et al., Progress on Synthesis of Glufosinate-Ammonium, Chemical World, 62(2): 65-70, 2021.
International Search Report in PCT/CN2022/089830 mailed on Jul. 27, 2022, 12 pages.

(Continued)

*Primary Examiner* — Iqbal H Chowdhury
(74) *Attorney, Agent, or Firm* — PORUS IP LLC

(57) ABSTRACT

Embodiments of the present disclosure relate to a D-amino acid oxidase mutant and application in preparing L-glufosinate thereof. The D-amino acid oxidase mutant has an amino acid substitution at at least one of position 62 and position 226 of an amino acid sequence of the D-amino acid oxidase mutant when compared to an amino acid sequence of a D-amino acid oxidase as set forth in SEQ ID NO. 1, the position 62 and position 226 being defined with reference to SEQ ID NO. 1, and the amino acid sequence of the D-amino acid oxidase mutant having at least 90% identity to SEQ ID NO. 1.

15 Claims, 4 Drawing Sheets
Specification includes a Sequence Listing.

(56) References Cited

OTHER PUBLICATIONS

Written Opinion in PCT/CN2022/089830 mailed on Jul. 27, 2022, 11 pages.
Tim Hawkes et al., D-Glufosinate as a Male Sterility Agent for Hybrid Seed Production, Plant Biotechnology Journal, 9(3): 301-314, 2011.
Jim-Min Fang et al., Enzymes in Organic Synthesis: Oxidoreductions, Journal of the Chemical Society, Perkin Transactions 1, 967-978, 1995.
Antonio Caligiuri et al., Multistep Enzyme Catalysed Deracemisation of 2-Naphthyl Alanine, Biocatalysis and Biotransformation, 24(6): 409-413, 2006.
First Office Action in Chinese Application No. 202110475238.X mailed on Mar. 13, 2024, 15 pages.

SEQUENCE LISTING

```
Sequence total quantity: 18
SEQ ID NO: 1            moltype = AA  length = 384
FEATURE                 Location/Qualifiers
source                  1..384
                        mol_type = protein
                        organism = Microbotryum intermedium
SEQUENCE: 1
MSSSTSSDKQ VVVIGAGVIG LTSALVLAQS NHNVTLVARD LPSDVSSQAF ASPWAGANWC   60
PFVDPQESVK NKRICDWETQ SFANFQQLIR EHGDGKLVMR LPARRYAENE KALLGHWYKS  120
VVPRYSTLPS SEVPNNGVGV EFETISVNAP LYCQWLEAQL LSHNATIIRR SLNSLDEALS  180
LAPSCSVIVN ATGLGAKSLG GVEDQTVTPI RGQTVLIKTD VKLCTMDASD PTKPSYIIPR  240
PGGEAVCGGC YGLGEWNLST DTELAKLILE RCLVLDPRIS SNGALDGIEV LRHNVGLRPS  300
RGTNEPRLEA ERVVLPSYSL NPHRRHALGA EGNAATVIHA YGVGPAGYQV SWGVANEVKA  360
LVDEHFAKFD TRTTQDGVHR DIKL                                        384

SEQ ID NO: 2            moltype = AA  length = 398
FEATURE                 Location/Qualifiers
source                  1..398
                        mol_type = protein
                        organism = Lactobacillus buchneri
SEQUENCE: 2
MTLVLAVLTP APVAGPPPLT VAAAIPLITH TPAGSTVPTP GGIAPLPGGL LGSVSGGLGL   60
LLTLGSLGVG PVVTSALGGP ASVPGLGLPT AAVVISGPPT PATLTAALIA LALLLLLAIT  120
AGIGSAHVAL AAAAGHAITV AGVTTSASVS VAGAGVMGLL ALVAAPIPAH AIVLAGGTAI  180
AAAVSAATAL GGMTVGVIGA GAIGAAVLGA LLPPGVLLVT AGAHGLPAGV GAGLGLTTPP  240
```

```
AVHGMVLVVA AVVLAAPLHA GTTHLPAAGV LATMLAGATI VAASAGGGVA AAAIVAALAS    300
GGIGGTSGAV TTPGPAPLAH PTATMPAGAM TPHMSGTTLS AGAATAAGAA GILGAPLGAL    360
PIAPGTLIAG GGSLAGTGAL STTVLLGGGT PGSGGAGL                            398

SEQ ID NO: 3            moltype = AA   length = 262
FEATURE                 Location/Qualifiers
source                  1..262
                        mol_type = protein
                        organism = Exiguobacterium sibiricum
SEQUENCE: 3
MGTASLLGLV AIVTGGSMGI GGAIIAATAG GGMAVVIATA SHPGGALLIA GAILGAGGGA     60
LTVGGAVSLG GAMIALVLGT VAHPGGLAVP VAAAGVGMPS PSHGMSLGAT GLVIAVALTG    120
APLGAAGALL TPVGHAVLGA IIAMSSVHGI IPTPTPVHTA ASLGGVLLMT GTLAMGTAPL    180
GIAIAAIGPG AIATPIAAGL PGAPLGAAAV GSMIPMGAIG LPGGISAVAA TLASAGASTV    240
TGITLPAAGG MTLTPSPGAG AG                                             262

SEQ ID NO: 4            moltype = AA   length = 252
FEATURE                 Location/Qualifiers
source                  1..252
                        mol_type = protein
                        organism = Lactobacillus brevis
SEQUENCE: 4
MSAALAGLVA IITGGTLGIG LAIATLPVGG GALVMITGAH SAVGGLAALS VGTPAGIGPP     60
GHASSAGAGT TLLPAATGLA PGPVSTLVAA AGIAVALSVG GTTTAGTALL LAVALAGVPP    120
GTALGIGAML ALGLGASIIA MSSIGGPVGA PSLGATAASL GAVAIMSLSA ALACALLATA    180
VAVATVHPGT ILTPLVAALP GAGGAMSGAT LTPMGHIGGP AAIATICVTL ASAGSLPATG    240
SGPVVAGGTT AG                                                        252

SEQ ID NO: 5            moltype = AA   length = 434
FEATURE                 Location/Qualifiers
source                  1..434
                        mol_type = protein
                        organism = Delftia acidovorans
SEQUENCE: 5
MQQPASAGVT NHAIPSYLQA DHLGPWGNYL QQVDRVTPYL GHLARWVETL KRPKRILIVD     60
VPIELDNGTI AHYEGYRVQH NLSRGPGKGG VRFHQDVTLS EVMALSAWMS VKNAAVNVPY    120
GGAKGGIRVD PKTLSRGELE RLTRRYTSEI GLLIGPSKDI PAPDVNTNGQ IMAWMMDTYS    180
MNTGATAGV VTGKPVDLGG SLGRVEATGR GVFTVGVEAA KLTGLSVQGA RIAVQGFGNV    240
GGTAGKLFAD VGAKVVAVQD HTGTIHNANG LDVPALLAHV AAKGGVGGFD GAEAMDAADF    300
WSVDCDILIP AALEGQITKE NAGKIKAKMV IEGANGPTTT EADDILTEKG VLVLPDVLAN    360
AGGVTVSYFE WVQDFSSFFW SEDEINARLV RIMQDAFAAI WQVAQQHGVT LRTATFIVAC    420
QRILHAREMR GLYP                                                      434

SEQ ID NO: 6            moltype = DNA   length = 1155
FEATURE                 Location/Qualifiers
source                  1..1155
                        mol_type = genomic DNA
                        organism = Microbotryum intermedium
SEQUENCE: 6
atgtcgtcaa gcacttcatc cgacaagcaa gtcgtcgtca ttggtgctgg tgttattggc     60
ctcacgtcgg cgctcgttct cgcgcagtcg aaccacaacg tcaccctcgt cgctcgccgg    120
ctcccctcgg atgtatcgtc ccaagcgttt gcctcacctt gggccggagc gaactggtgc    180
cccttttgtg acccgcaaga atcggtcaag aacaaggaga tctgcgactg ggagacgcag    240
tcgttcgcaa acttccagca actcataaga gaacacggcg atggcaaact cgtcatgagg    300
cttcgggcga ggagatacgc cgagaacgaa aaagccctcc tggggcattg gtacaaatca    360
gtcgtgccta gatactcgac cttgccctcg tccgaggtcc caacaacgg cgtcggcgtc    420
gaattcgaga ccatctcggt taacgcgccg ctctactgcc aatggctcga ggctcaactc    480
ttgtctcaca acgccaccat catccgccgc tcgctcaact ccctcgacga ggccttgtcg    540
ctcgcacctt cttgctcggt catcgtcaac gccaccgggc tcggcgccaa atcactcgga    600
gggagtcgag atcagacggt caccccatc cgagggcaga ccgtcttgat caagaccgac    660
gtcaagctgt gcactatgga tgcgtcagac cccaccaaac cgtcctatat cattccgagg    720
ccaggggggcg aggccgtttg tggtggttgc tacggcctcg gggaatgaaa tctctccacc    780
gatacggaac tggccaagct gattctcgaa cgatgcctgg tgctcgaccc ccgcatctca    840
tccaatggtg gccttgacgg catcgaagtg cttgcacaca tgtcggggct gcggccatca    900
cgaggcacga atgaacccag gctagaggcc gaacgagtcg tccttccttc ctattctttg    960
aaccctcatc gaaggcatgc gctcggtgca gagggcaacg ccgcgacggt cattcacgcc   1020
tacggggtcg ggccggcagg atatcaagtc agctggggg tcgcgaacga ggtgaaagcg   1080
ctagtcgacg aacacttcgc caagtttgac actcgaacga cccaagacgg cgtccaccgg   1140
gacattaaac tctag                                                    1155

SEQ ID NO: 7            moltype = DNA   length = 1197
FEATURE                 Location/Qualifiers
source                  1..1197
                        mol_type = genomic DNA
                        organism = Lactobacillus buchneri
SEQUENCE: 7
atgaccaaag ttctggccgt gctgtatccg gatccggtgg atggttttcc gccgaaatat     60
gttcgtgatg atattccgaa aatcacccat tatccggatg cagtaccgt tccgaccccg    120
gaaggcattg attttaaacc gggtgaactg ctgggtagcg ttagtggcgg tctgggcctg    180
```

-continued

```
aaaaaatatc tggaaagtaa aggtgtggaa tttgttgtta ccagtgataa agaaggcccg   240
gatagtgtgt ttgaaaaaga actgccgacc gccgatgtgg ttattagtca gccgttttgg   300
ccggcctatc tgaccgcaga tctgattgat aaagcaaaaa agctgaaact ggcaattacc   360
gccggtattg cagcgatca tgtggatctg aatgccgcca atgaacataa tattaccgtt   420
gcagaagtga cctatagcaa tagtgttagt gttgcagaaa cagaagtgat gcagctgctg   480
gccctggtgc gtaattttat tccggcacat gatattgtga agccggtgg ctggaatatt   540
gcagatgcag ttagccgtgc ctatgatctg aaggtatga ccgttggtgt gattggtgca   600
ggccgcattg gtcgtgccgt tctggaacgt ctgaaaccgt tggcgttaa actggtgtat   660
aatcagcgcc atcagctgcc ggatgaagtt gaaaatgaac tgggcctgac ctattttccg   720
gatgttcatg aaatggtgaa agttgtggat gccgttgttc tggcagcacc gctgcatgca   780
cagacctatc atctgtttaa tgatgaagtt ctggccacca tgaaacgtgg cgcctatatt   840
gtgaataata gccgcggcga agaagttgat cgcgatgcaa ttgttcgcgc actgaatagc   900
ggtcagattg gcggttatag tggcgatgtt tggtatccgc agccggcacc gaaagatcat   960
ccgtggcgta ccatgccgaa tgaagcaatg accccgcata tgagtggcac caccctgagt  1020
gcccaggcac gctatgccgc aggtgcacgt gaaattctgg aagattttct ggaagataaa  1080
ccgattcgtc cggaatatct gattgcccag ggtggtagtc tggccggtac cggtgccaaa  1140
agttataccg tgaaaaaagg cgaagaaacc ccgggtagcg cgaagcaga aaaataa     1197

SEQ ID NO: 8             moltype = DNA   length = 789
FEATURE                  Location/Qualifiers
source                   1..789
                         mol_type = genomic DNA
                         organism = Exiguobacterium sibiricum
SEQUENCE: 8
atgggttata attctctgaa aggcaaagtc gcgattgtta ctggtggtag catgggcatt    60
ggcgaagcga tcatccgtcg ctatgcagaa gaaggcagtg gcgttgttat caactatcgt   120
agccatccgg aggaagccaa aaagatcgcc gaagatatta acaggcagg tggtgaagcc   180
ctgaccgtcc agggtgacgt ttctaaagag aagacatga tcaacctggt gaaacagact   240
gttgatcact tcggtcagct ggacgtcttt gtgaacaacg ctggcgttga gatgccttct   300
ccgtcccacg aaatgtccct ggaagactgg cagaaagtga tcgatgttaa tctgacgggt   360
gcgttcctgg gcgctcgtga agctctgaaa tacttcgttg aacataacgt gaaaggcaac   420
attatcaata tgtctagcgt ccacgaaatc atcccgtggc ctactttcgt acattacgct   480
gcttctaagg gtgcgttaa actgatgacc cagactctgg ctatgaata tgcaccgaaa   540
ggtatccgca ttaacgctat cggtccaggc gcgatcaaca ctccaattaa tgcagaaaaa   600
ttcgaggatc cgaaacagcg tgcagacgtg gaaagcatga tccccgatggg caacatcggc   660
aagccagagg atttccgc tgtcgcggca tggctggctt ctgacgaagc gtcttacgtt   720
accggcatca ccctgttcgc agatggtggc atgacctgt accgagctt tcaggctggc   780
cgtggttga                                                          789

SEQ ID NO: 9             moltype = DNA   length = 759
FEATURE                  Location/Qualifiers
source                   1..759
                         mol_type = genomic DNA
                         organism = Lactobacillus brevis
SEQUENCE: 9
atgagcaacc gtctggacgg caaggtggcg atcattaccg gtggcaccct gggtattggt    60
ctggcgattg cgaccaagtt cgtggaggaa ggtgcgaaag ttatgatcac ggtccgtcac   120
agcgacgtgg cgagaaggc ggcgaaaagc gttggcaccc cggaccagat tcaattcttt   180
cagcacgata cagcgacga ggatggttgg accaagctgt tcgatgcgac cgaaaaagcg   240
tttggcccgt tagcacccct ggttaacaac gcgggtattg cggtgaacaa gagcgttgag   300
gaaaccacca ccgcggagtg gcgtaaactg ctggccgtga acctggatgg tgtttttcttt   360
ggcacccgtc tgggtatcca acgtatgaag aacaaaggtc tgggcgcgag catcattaac   420
atgagcagca ttgaaggtt cgttggtgac ccgagcctgg gtcgtacaa cgcgagcaag   480
ggtgcggttc gtatcatgag caaaagcgcg gcgctggatt gcgcgctgaa ggactacgat   540
gtgcgtgtta acaccgtgca ccccggggcta ttaaaaaccc tggtggttga cgatctgccg   600
ggtgcggagg aagcgatgag ccagcgtacc aagaccccga tggtcacat gcgcgaaccg   660
aacgacatcg cgtacatttg cgtttatctg gcgagcaacg agagcaaatt cgcgaccggt   720
agcgaatttg tggttgatgg tggctatacc gcgcaataa                         759

SEQ ID NO: 10            moltype = DNA   length = 1305
FEATURE                  Location/Qualifiers
source                   1..1305
                         mol_type = genomic DNA
                         organism = Delftia acidovorans
SEQUENCE: 10
atgcagcaac ccgcttcggc cggcgttacc aaccacgcca tcccttccta cctgcaggcc    60
gatcacctcg gcccctgggg caactacctg cagcaggtcg atcgcgtcac gccctacctg   120
ggccatctcg cccgctgggt cgaaacccct aagcgccca agcgcatcct gatcgtcgat   180
gtgccgatcg agctggacaa cggccaccatc gcccactacg aaggctaccg cgtgcagcac   240
aacctgagcc gcggtcccgg caagggcggc gtgcgtttcc accaggacgt gaccctgtcc   300
gaagtcatgg ccctgtcggc ctggatgtcg gtcaagaacg cggccgtcaa cgtgccctat   360
ggtggcgcca agggcggcat ccgtgtcgat cccaagacgc tgtcgcgcgg tgagctggag   420
cgcctgacgc gccgctacac cagcgagatc ggccctgcta tcggccccctc caaggacatc   480
cccgcgcctg acgtcaacac caatggccag atcatggcct ggatgatgga cactactccg   540
atgaacaccg cgccaccgc caccggcgtg tcacgggca agccccgtgga cctgggcggc   600
tcgctgggcc gcgtcgaggc caccggccgc ggcgttca ccgtgggcgt ggaagcggcc   660
aagctgaccg gcctgtcggt ccagggcgcg cgcatcgccg tgcagggctt cggcaacgtg   720
ggcggcacgg cgggcaagct gttcgccgac gtgggcgcca aggtcgtggc cgtgcaggac   780
cacaccggca ccatccacaa cgccaatggc ctggacgtgc cggcccctgct ggcccacgtg   840
```

```
gctgccaagg gcggcgtggg cggctttgac ggcgccgagg ccatggacgc tgccgacttc    900
tggagcgtgg actgcgacat cctgatcccc gccgcactgg aaggccagat caccaaggaa    960
aacgccggca agatcaaggc caagatggtg atcgagggcg ccaacggccc caccaccacc   1020
gaggccgacg acatcctgac cgaaaagggc gtgctggtgc tgcccgatgt gctggccaat   1080
gccggcgccg tgacggtgag ctacttcgaa tgggtgcaga acttctccag cttcttctgg   1140
agcgaggacg agatcaacgc ccgcctggtg cgcatcatgc aggacgcctt cgcggccatc   1200
tggcaggtcg cccagcagca cggcgtgacg ctgcgcaccg ccaccttcat cgtggcctgc   1260
cagcgcatcc tgcatgcgcg cgagatgcgg ggactgtatc cctga                   1305

SEQ ID NO: 11          moltype = DNA  length = 37
FEATURE                Location/Qualifiers
source                 1..37
                       mol_type = other DNA
                       organism = synthetic construct
SEQUENCE: 11
gattcttgcg ggtccacctt ggggcaccag ttcgctc                               37

SEQ ID NO: 12          moltype = DNA  length = 37
FEATURE                Location/Qualifiers
source                 1..37
                       mol_type = other DNA
                       organism = synthetic construct
SEQUENCE: 12
gagcgaactg gtgccccaag gtggacccgc aagaatc                               37

SEQ ID NO: 13          moltype = DNA  length = 33
FEATURE                Location/Qualifiers
source                 1..33
                       mol_type = other DNA
                       organism = synthetic construct
SEQUENCE: 13
ggggtctgac gcatcggtag tgcacagctt gac                                   33

SEQ ID NO: 14          moltype = DNA  length = 33
FEATURE                Location/Qualifiers
source                 1..33
                       mol_type = other DNA
                       organism = synthetic construct
SEQUENCE: 14
gtcaagctgt gcactaccga tgcgtcagac ccc                                   33

SEQ ID NO: 15          moltype = DNA  length = 29
FEATURE                Location/Qualifiers
source                 1..29
                       mol_type = other DNA
                       organism = synthetic construct
SEQUENCE: 15
cctggtggaa acggatgccg cccttgccg                                        29

SEQ ID NO: 16          moltype = DNA  length = 29
FEATURE                Location/Qualifiers
source                 1..29
                       mol_type = other DNA
                       organism = synthetic construct
SEQUENCE: 16
cggcaagggc ggcatccgtt tccaccagg                                        29

SEQ ID NO: 17          moltype = DNA  length = 31
FEATURE                Location/Qualifiers
source                 1..31
                       mol_type = other DNA
                       organism = synthetic construct
SEQUENCE: 17
gggtccgaag aatcggtcgt gcagcgcttg c                                     31

SEQ ID NO: 18          moltype = DNA  length = 31
FEATURE                Location/Qualifiers
source                 1..31
                       mol_type = other DNA
                       organism = synthetic construct
SEQUENCE: 18
gcaagcgctg cacgaccgat tcttcggacc c                                     31
```

D-AMINO ACID OXIDASE MUTANTS AND USES THEREOF IN PREPARING L-GLUFOSINATE

CROSS REFERENCE TO RELATED APPLICATIONS

This application is a continuation of International Application No. PCT/CN2022/089830, filed on Apr. 28, 2022, which claims priority to Chinese Patent Application No. 202110475247.9, filed on Apr. 29, 2021, the entire contents of which are hereby incorporated by reference.

SEQUENCE LISTING

The instant application contains a Sequence Listing which has been submitted electronically in XML format and is hereby incorporated by reference in its entirety. The XML copy, created on Sep. 13, 2023, is named "2023-09-13-Sequence list-64701-H001US00-MLT," and is 23,620 bytes in size.

TECHNICAL FIELD

The present disclosure relates to the field of biotechnology, and in particular, to a D-amino acid oxidase mutant, application of the D-amino acid oxidase mutant in preparing L-glufosinate, and a method for preparing the L-glufosinate using the D-amino acid oxidase mutant.

BACKGROUND

The herbicide glufosinate (also known as bialaphos, phosphinothricin (PPT), or 2-amino-4-(hydroxymethylphosphinyl)butyric acid, a corresponding product name including basta, etc.) is a non-selective contact-type organophosphorus herbicide with low toxicity and high efficiency, which is developed by Hoechst (now part of the Bayer Corporation) in Germany in the 1980s. After acting on plants, the glufosinate can inhibit glutamine synthetase to interrupt reversible reactions of glutamic acid in the plants, causing a metabolic disorder and poisoning the plant due to an excessive accumulation of ammonia, at the same time, the plants are unable to synthesize chlorophyll, which inhibits photosynthesis of the plants, resulting in the death of the plants. The glufosinate is mainly used in orchards, potato fields, non-cultivated land, etc. for preventing and controlling annual and perennial gramineous and dicotyledonous weeds (e.g., crabgrass, *Setaria viridis*, wild wheat, etc.) and perennial gramineous weeds and sedges (e.g., fescue, duck sprouts, etc.).

The market for sterilant herbicides is huge. Currently, three major herbicides are paraquat, glyphosate, and glufosinate in the world. The glyphosate dominates the market in terms of use, but a large number of weeds develops resistance due to its long-term use, and the glyphosate tends to become ineffective. The paraquat has been included in the Rotterdam Convention due to its high toxicity, which is banned or restricted by more and more countries around the world. The Ministry of Agriculture of China has issued an announcement stating that the production of paraquat has been discontinued from Jul. 1, 2014 and the use of paraquat has been banned from usage from Jul. 1, 2016. At present, although the production of the glufosinate is small, it has excellent herbicidal performance and fewer side effects, therefore, the glufosinate has a huge market potential in the future.

There are two optical isomers of the glufosinate (L-glufosinate and D-glufosinate), but only the L-glufosinate has herbicidal activity and is easily decomposed in the soil, with less toxicity to humans and animals, a broad herbicide controlling spectrum, and less destructive to the environment.

At present, the glufosinate sold in the market is generally a racemic mixture. If the glufosinate merely includes a pure optical isomer of L-glufosinate, a usage amount of the glufosinate may be significantly reduced, which is of great significance for improving atom economy, reducing cost, and alleviating the pressure on the environment.

There are three main manners for preparing a pure L-glufosinate, including chiral resolution, chemical synthesis, and biocatalysis.

The chiral resolution requires using an expensive resolution agent (e.g., quinine) with cumbersome resolution steps (e.g., salt formation, induced crystallization, and desalting), and a theoretical yield of the chiral resolution is only 50%, which leads to a relatively low industrial value of this manner.

The chemical synthesis includes asymmetric synthesis and natural amino acid chiral pool, etc. Drawbacks of this manner include needing expensive precious metals and ligands, highly toxic substances for starting materials or reaction routes, or a long reaction and synthesis route, etc.

However, the biocatalysis has advantages of strict stereoselectivity, a mild reaction condition, and a high yield, which is an advantageous manner for producing the L-glufosinate. The biocatalysis mainly includes (1) obtaining the glufosinate by using derivatives of the L-glufosinate as a substrate and performing enzymatic hydrolysis directly, which has main advantages of a high conversion rate and a high enantiomeric excess of the obtained product, but needs expensive and not-easily-obtained chiral raw materials as precursors; (2) obtaining the glufosinate by using a precursor of a racemic glufosinate as the substrate and performing selective enzymatic resolution, which has main advantages of relatively easily obtained raw materials and a high vitality catalyst, but a theoretical yield of which may only reach 50%, resulting in waste of the raw materials.

In addition to these two traditional biocatalysis, a de-racemic synthesis highlights a significant cost advantage using the D, L-glufosinate as raw materials. Since the sold glufosinate is the D, L-glufosinate, the industrial production technology of which is very mature, the de-racemic synthesis directly uses the D, L-glufosinate as raw materials, which has a low cost and is better connected to the existing industrial production system of the glufosinate.

SUMMARY

One of the embodiments of the present disclosure provides a D-amino acid oxidase mutant. The D-amino acid oxidase mutant has an amino acid substitution at at least one of position 62 and position 226 of an amino acid sequence of the D-amino acid oxidase mutant when compared to an amino acid sequence of a D-amino acid oxidase as set forth in SEQ ID NO. 1, the position 62 and position 226 are defined with reference to the SEQ ID NO. 1, and the amino acid sequence of the D-amino acid oxidase mutant has at least 90% identity to the SEQ ID NO. 1.

In some embodiments, methionine at the position 226 may be substituted with threonine.

In some embodiments, phenylalanine at the position 62 may be substituted with lysine.

In some embodiments, the D-amino acid oxidase mutant may be derived from *Microbotryum intermedium*.

In some embodiments, the D-amino acid oxidase mutant may have an amino acid sequence having at least 99% identity to the SEQ ID NO. 1.

One embodiment of the present disclosure provides a nucleic acid encoding the D-amino acid oxidase mutant.

One embodiment of the present disclosure provides an expression vector comprising the nucleic acid.

One embodiment of the present disclosure provides a recombinant host cell comprising the nucleic acid.

In some embodiments, the host cell may be derived from one of *Saccharomyces cerevisiae, Yarrowia lipolitica, Candida krusei, Issatchenkia orientalis*, Actinomycetes, *Streptomyces, Bacillus subtilis*, or *Escherichia coli*.

One of the embodiments of the present disclosure provides a method for preparing L-glufosinate, the method comprising generating L-glufosinate by converting D-glufosinate in the presence of an enzymatic system. The enzymatic system comprises the D-amino acid oxidase mutant for converting D-glufosinate to 4-(Methylhydroxyphosphinyl)-2-oxobutyric acid; and the D-glufosinate is initially present in a racemic mixture of D-glufosinate and L-glufosinate or salts thereof.

In some embodiments, the enzymatic system may further comprise an L-amino acid dehydrogenase for converting 4-(Methylhydroxyphosphinyl)-2-oxobutyric acid to the L-glufosinate.

In some embodiments, the enzymatic system may further comprise catalase.

In some embodiments, the enzymatic system may further comprise a coenzyme recycling system, and the coenzyme recycling system may be selected from at least one of a formate dehydrogenase coenzyme recycling system, a glucose dehydrogenase coenzyme recycling system, and an alcohol dehydrogenase coenzyme recycling system.

The formate dehydrogenase coenzyme recycling system may comprise a formate dehydrogenase, formate and a coenzyme.

The glucose dehydrogenase coenzyme recycling system may comprise a glucose dehydrogenase, glucose and a coenzyme.

The alcohol dehydrogenase coenzyme recycling system may comprise an alcohol dehydrogenase, isopropanol and a coenzyme.

In some embodiments, each enzyme in the enzymatic system may be obtained independently from a free enzyme and a recombinant host cell expressing the enzyme.

In some embodiments, the recombinant host cell may be selected from: *Saccharomyces cerevisiae, Yarrowia lipolitica, Candida krusei, Issatchenkia orientalis*, Actinomycetes, *Streptomyces, Bacillus subtilis* or *Escherichia coli*.

In some embodiments, a total addition of the recombinant host cell may be 1-200 g/L by weight of wet cells in a reaction solution for a conversion reaction.

In some embodiments, the reaction solution for the conversion reaction may have a pH of 7-10.

In some embodiments, the reaction solution may have a pH of 8-9.

In some embodiments, the D-amino acid oxidase mutant may catalyze an oxidation reaction at a reaction temperature of 25-45° C. for 6-24 h.

DETAILED DESCRIPTION

Figure 1:
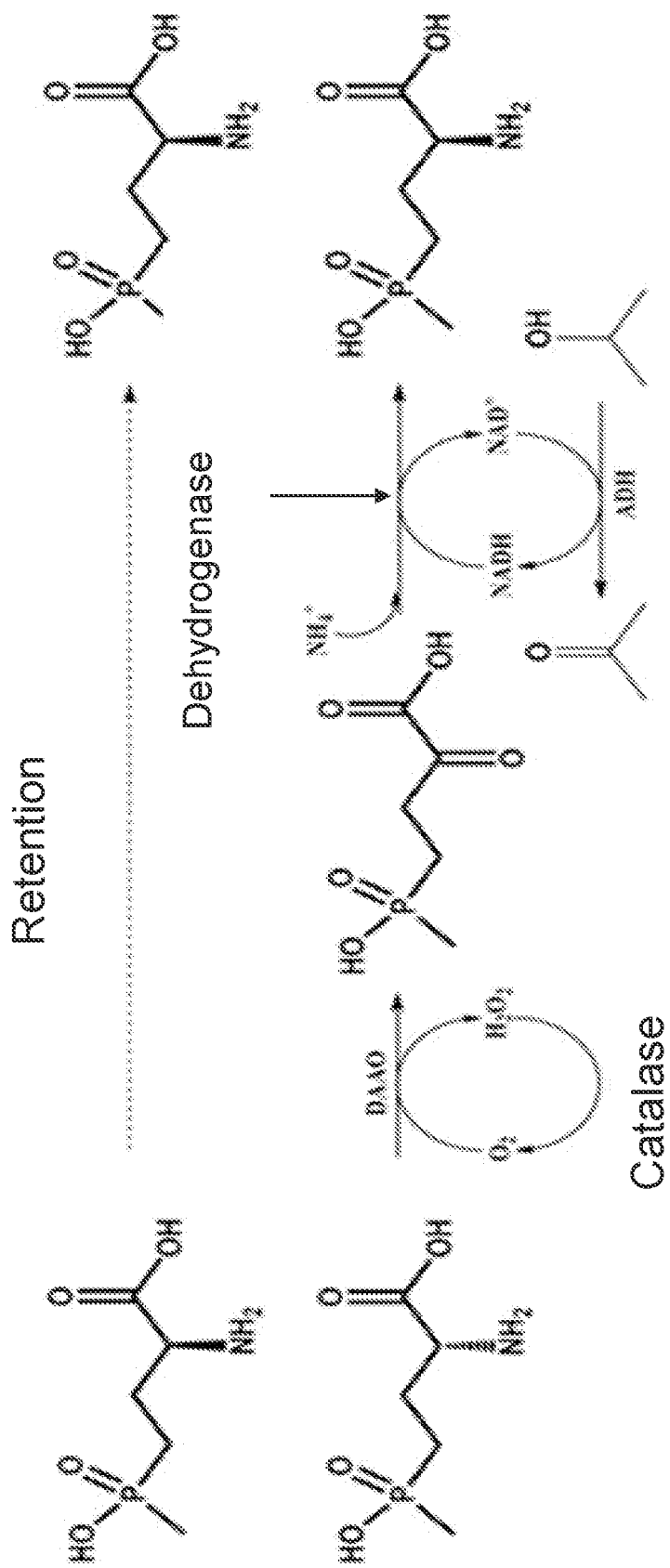
FIG. 1 illustrates an exemplary reaction formula for preparing L-glufosinate by a multi-enzyme system resolution manner according to some embodiments of the present disclosure.

As indicated in the present disclosure and in the claims, unless the context clearly suggests an exception, the words "one," "a," "a kind of," and/or "the" do not refer specifically to the singular but may also include the plural. In general, the terms "including" and "comprising" suggest only the inclusion of clearly identified steps and elements, which do not constitute an exclusive list, and the method may also include other steps or elements.

Unless otherwise defined, all technical and scientific terms used herein have the same meaning as commonly understood by those of ordinary skill in the art to which the present disclosure belongs.

According to the embodiments of the present disclosure, a D-amino acid oxidase mutant may be used to improve the bio-enzymatic production of L-glufosinate based on its identification.

Embodiments of the present disclosure provide a D-amino acid oxidase mutant having a D-amino acid oxidase (DAAO) activity. When compared to an amino acid sequence of a D-amino acid oxidase as set forth in SEQ ID NO. 1, the D-amino acid oxidase mutant has an amino acid substitution at at least one of position 62 and position 226 of an amino acid sequence of the D-amino acid oxidase mutant, the position 62 and position 226 are defined with reference to the SEQ ID NO. 1, and the amino acid sequence of the D-amino acid oxidase mutant has at least 90% identity to the SEQ ID NO. 1.

In some embodiments, phenylalanine (F) at the position 62 may be substituted with lysine (K), which may be represented by F62K, i.e., F at the position 62 is substituted with K.

In some embodiments, methionine (M) at the position 226 may be substituted with threonine (T), which may be represented by M226T, i.e., M at the position 226 is substituted with T.

In some embodiments, the D-amino acid oxidase mutant may comprise an amino acid substitution represented by F62K when compared to the amino acid sequence of the D-amino acid oxidase as set forth in the SEQ ID NO. 1, wherein a position of the amino acid may be defined with reference to the SEQ ID NO. 1.

In some embodiments, the D-amino acid oxidase mutant may comprise an amino acid substitution represented by M226T when compared to the amino acid sequence of the D-amino acid oxidase as set forth in the SEQ ID NO. 1, wherein the position of the amino acid may be defined with reference to the SEQ ID NO. 1.

In some embodiments, the D-amino acid oxidase mutant may comprise the amino acid substitutions represented by F62K and M226T when compared to the amino acid sequence of the D-amino acid oxidase as set forth in the SEQ ID NO. 1, wherein the position of the amino acid position may be defined with reference to the SEQ ID NO. 1.

In embodiments of the present disclosure, the amino acid sequence of the D-amino acid oxidase as set forth in the SEQ ID NO. 1 may be referred to as a wild-type enzyme having a D-amino acid oxidase activity. The wild-type enzyme may have a nucleotide sequence as set forth in SEQ ID NO.6.

The term "mutant" as used in the embodiments of the present disclosure refers to a polynucleotide or polypeptide that contains an alteration at one or more positions relative to a comparable polynucleotide or polypeptide (e.g., the wild-type enzyme having the D-amino acid oxidase activity). The alteration may include a substitution, deletion, and/or insertion of a nucleotide and the amino acid. The "D-amino acid oxidase mutant" described in the embodiments of the present disclosure has the D-amino acid oxidase activity, i.e., an activity of converting a D-amino acid to ammonia, keto acids (a type of which is determined by a substrate of the D-amino acid), and hydrogen peroxide. Particularly, the D-amino acid oxidase mutant in the present disclosure has an activity of converting D-glufosinate to 4-(Methylhydroxyphosphinyl)-2-oxobutyric acid.

"The position of the amino acid is defined with reference to SEQ ID NO. 1" means that an amino acid in the D-amino acid oxidase mutant aligns to the amino acid at a specific position (e.g., the position 62 or position 226) when compared to the amino acid sequence as set forth in SEQ ID NO. 1.

The D-amino acid oxidase mutant of the embodiments of the present disclosure can have an improved activity compared to the wild-type enzyme having the D-amino acid oxidase activity. For example, the D-amino acid oxidase mutant may have a higher catalytic efficiency in a catalytic reaction for converting the D-glufosinate to the 4-(Methylhydroxyphosphinyl)-2-oxobutyric acid and higher efficiency in the utilization of oxygen. Optionally, the D-amino acid oxidase mutant may have a better stability for use, etc., in biocatalysis for producing the L-glufosinate, especially in the biocatalysis described in the embodiments of the present disclosure.

The term "catalytic efficiency" as used in the embodiments of the present disclosure refers to an index that reflects an enzyme catalytic capacity of the D-amino acid oxidase. In some embodiments, the catalytic efficiency refers to an extent or a rate at which the D-amino acid oxidase is able to convert the D-glufosinate to the 4-(Methylhydroxyphosphinyl)-2-oxobutyric acid.

In some embodiments, the catalytic efficiency of the D-amino acid oxidase mutant of the present disclosure may be enhanced as compared to the wild-type enzyme or a reference D-amino acid oxidase. Preferably, the catalytic efficiency of the D-amino acid oxidase mutant of embodiments of the present disclosure may be at least 1.5, 1.6, 1.7, 1.8, 1.9, 2.0, 2.1, 2.2, 2.3, 2.4, 2.5, 2.6, 2.7, 2.8, 2.9, 3.0, or 3.1 times of the wild-type enzyme or the reference D-amino acid oxidase.

In some embodiments, the D-amino acid oxidase mutant may be derived from *Microbotryum intermedium*.

In some embodiments, the amino acid sequence of the D-amino acid oxidase mutant may have at least 90%, 91%, 92%, 93%, 94%, 95%, 96%, 97%, 98%, or 99% identity to the SEQ ID NO. 1. In some embodiments, a nucleotide sequence of the D-amino acid oxidase mutant may have at least 90%, 91%, 92%, 93%, 94%, 95%, 96%, 97%, 98%, or 99% identity to SEQ ID NO. 6. In some embodiments, the D-amino acid oxidase mutant may comprise an amino acid sequence having one or more (e.g., 1, 2, 3, 4, 5, 6, 7, 8, 9, or 10) amino acid substitutions, amino acid deletions, and/or amino acid insertions as compared to the wild-type enzyme and/or have one or more truncated amino acid sequences as compared to the wild-type enzyme.

In some embodiments, when compared to the amino acid sequence of the D-amino acid oxidase as set forth in the SEQ ID NO. 1, the amino acid substitution of the D-amino acid oxidase mutant may be amino acid substitution at the position 226 and amino acid substitution at the position 62.

Embodiments of the present disclosure also provide a nucleic acid or a polynucleotide sequence encoding the D-amino acid oxidase mutant described above. The nucleic acid or polynucleotide sequence may be isolated.

The term "nucleic acid" or "polynucleotide" includes a DNA molecule (e.g., cDNA or genomic DNA) and an RNA molecule (e.g., mRNA) and an analog of DNA or RNA produced using a nucleotide analog. A nucleic acid molecule may be single-stranded or double-stranded, preferably, the nucleic acid molecule may be double-stranded.

Embodiments of the present disclosure also provide an expression vector comprising the nucleic acid or polynucleotide sequence as described above. The term "expression vector" may comprise an operable connection with one or more control sequences, the one or more control sequences being capable of directing an expression of the D-amino acid oxidase mutant in a suitable expression host.

The term "operable connection" refers to a linkage of polynucleotide elements (coding sequences or nucleic acid sequences) in a functional relationship. A nucleic acid sequence is "operably linked" when it is placed in a functional relationship with another nucleic acid sequence. For example, if a promoter or enhancer affects a transcription of a coding sequence, the nucleic acid sequence is operably linked to the coding sequence. In some embodiments, the control sequence may comprise the promoter, the enhancer, a terminator, etc.

The term "expression vector" refers to any vector (e.g., plasmid or virus) that facilitates a recombinant DNA process and causes an expression of a target polynucleotide. The expression vector of embodiments of the present disclosure comprises a nucleic acid sequence encoding the D-amino acid oxidase mutant to enable an expression of the D-amino acid oxidase mutant. The expression vector is usually selected based on a compatibility of a vector with cells to be introduced into the vector. The expression vector may be a vector that exists as an extrachromosomal entity and whose replication is independent of chromosomal replication, for example, a plasmid, an extrachromosomal element, a micro chromosome or an artificial chromosome. Alternatively, the expression vector may be a vector that is integrated into a genome when introduced into the host cell and replicates with chromosomes which has been integrated into the genome.

In some embodiments, more than one (e.g., 2, 3, or 4) copy expression vectors may be inserted into a host cell to increase production of the D-amino acid oxidase mutant encoded by the nucleic acid sequence contained in the host cell (causing the host cell to overexpress the D-amino acid oxidase mutant).

In some embodiments, the expression vector may further comprise a nucleic acid sequence encoding a formate dehydrogenase, a glucose dehydrogenase, or an alcohol dehydrogenase to enable expression of these dehydrogenases with a mutant. Preferably, these dehydrogenases enable co-expression with an L-amino acid dehydrogenase mutant.

Embodiments of the present disclosure also provide a recombinant host cell comprising the nucleic acid or the expression vector as described above.

In some embodiments, the recombinant host cell may be a prokaryotic cell or a eukaryotic cell. In some embodiments, the host cell may be derived from one of *Saccharomyces, Aspergillus, Pichia, Kluyveromyces, Candida, Hansenula, Humicola, Issatchenkia, Trichosporon, Brettanomyces, Pachysolen, Yarrowia, Actinomycetes, Streptomyces, Bacillus*, or *Escherichia*. Preferably, the host cell may be derived from one of *Saccharomyces cerevisiae, Yarrowia lipolitica, Candida krusei, Issa orientalis, Bacillus subtilis* or *Escherichia coli*.

In some embodiments, the expression vector of embodiments of the present disclosure may be introduced into the prokaryotic cell or the eukaryotic cell by conventional transformation or transfection techniques.

The terms "transformation" and "transfection" refer to a variety of techniques recognized in the art for introducing a foreign nucleic acid (e.g., DNA) into the host cell. Available manners for transforming and transfecting the host cell may be referred to Sambrook, etc. (Molecular Cloning: A Laboratory Manual, $2^{nd}$ edition. Cold Spring Harbor Laboratory, Cold Spring Harbor Laboratory Press, Cold Spring Harbor, N Y, 1989), Davis, Basic Methods in Molecular Biology (1986) and other laboratory manuals.

In some embodiments, the recombinant host cell may be a host cell co-expressing (a) and (b): (a) the L-amino acid dehydrogenase with activity of converting 4-(Methylhydroxyphosphinyl)-2-oxobutyric acid to the L-glufosinate; and (b) a dehydrogenase derived from the formate dehydrogenase, the glucose dehydrogenase, or the alcohol dehydrogenase.

Embodiments of the present disclosure also provide uses of the D-amino acid oxidase mutant, the nucleic acid, the expression vector, or the recombinant host cell described in some embodiments of the present disclosure in preparing the L-glufosinate.

Embodiments of the present disclosure also provide a method for preparing the L-glufosinate, comprising: generating the L-glufosinate by converting the D-glufosinate in the presence of an enzymatic system, and the enzymatic system comprises the D-amino acid oxidase mutant for converting the D-glufosinate to the 4-(Methylhydroxyphosphinyl)-2-oxobutyric acid.

In some embodiments, the D-glufosinate may be initially present in a racemic mixture of D-glufosinate and L-glufosinate or salts thereof. Starting materials for racemic glufosinate are available in a variety of forms, for example, various salts of the racemic glufosinate, e.g., ammonium and hydrochloride salts, or amphoteric ions of the racemic glufosinate.

In some embodiments, the enzymatic system may further comprise the L-amino acid dehydrogenase for converting the 4-(Methylhydroxyphosphinyl)-2-oxobutyric acid to the L-glufosinate. In some embodiments, the L-amino acid dehydrogenase may be a Glu/Leu/Phe/Val dehydrogenase. The L-amino acid dehydrogenase or the Glu/Leu/Phe/Val dehydrogenase may be any enzyme known in the art having an L-amino acid dehydrogenase activity or a Glu/Leu/Phe/Val dehydrogenase activity or variants thereof. For example, the L-amino acid dehydrogenase may be an L-amino acid dehydrogenase described in the applications with Patent Application No. CN109750009B, CN109609475B, and CN110791484B.

In some embodiments, the enzymatic system may further comprise a catalase, which is used to remove a by-product of hydrogen peroxide since an accumulation of the hydrogen peroxide has a toxic effect on the enzyme catalyst. The catalase may be any enzyme known in the art having a catalase activity. For example, the catalase may be purchased from Ningxia Xiasheng Industrial Group Co., Ltd., with a trade number of CAT-400.

In some embodiments, the enzymatic system may further comprise a coenzyme recycling system which is selected from at least one of a formate dehydrogenase coenzyme recycling system, a glucose dehydrogenase coenzyme recycling, and an alcohol dehydrogenase coenzyme recycling system:

a. The formate dehydrogenase coenzyme recycling system may comprise the formate dehydrogenase, formate and a coenzyme;
b. The glucose dehydrogenase coenzyme recycling may comprise the glucose dehydrogenase, glucose and a coenzyme;
c. The alcohol dehydrogenase coenzyme recycling system may comprise the alcohol dehydrogenase, isopropanol and a coenzyme.

In preferred embodiments, the coenzyme may be NADH.

Figure 2:
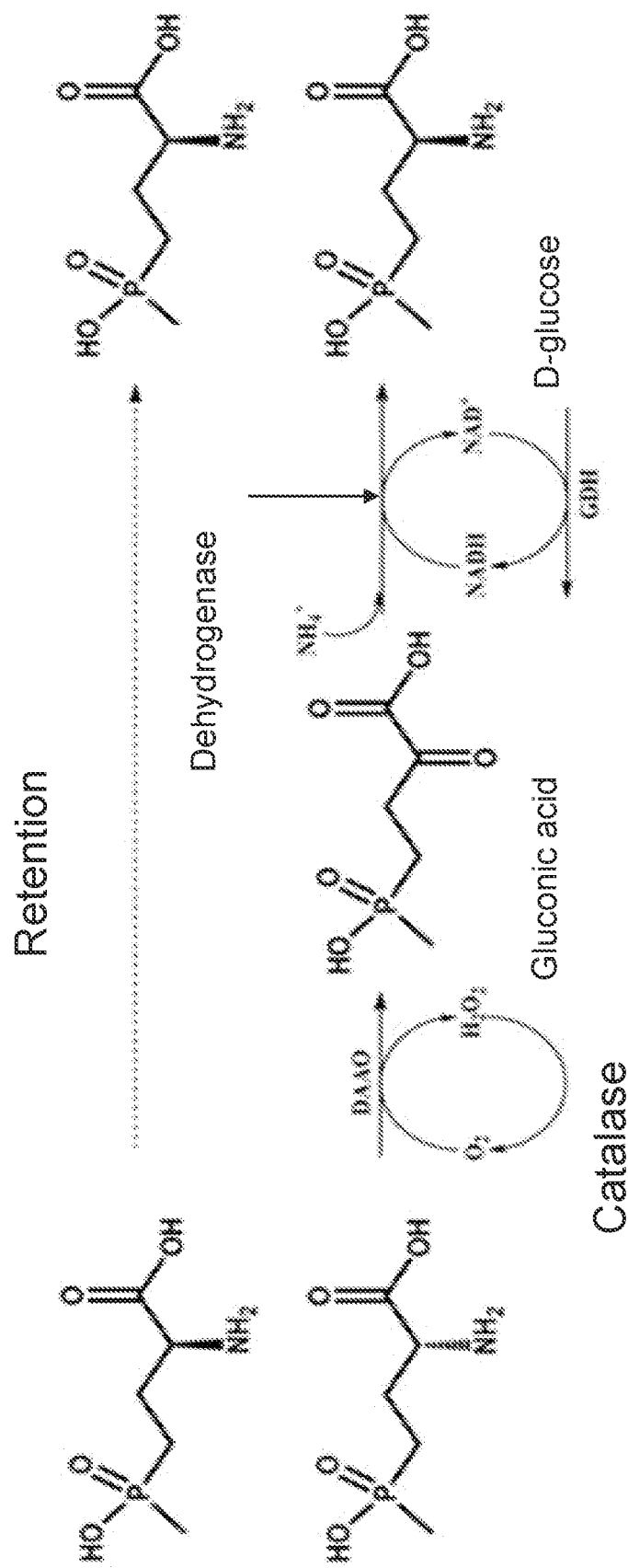
FIG. 2 illustrates an exemplary reaction formula for preparing the L-glufosinate by deracemization (with a glucose dehydrogenase coenzyme recycling system) according to some embodiments of the present disclosure.
Figure 3:
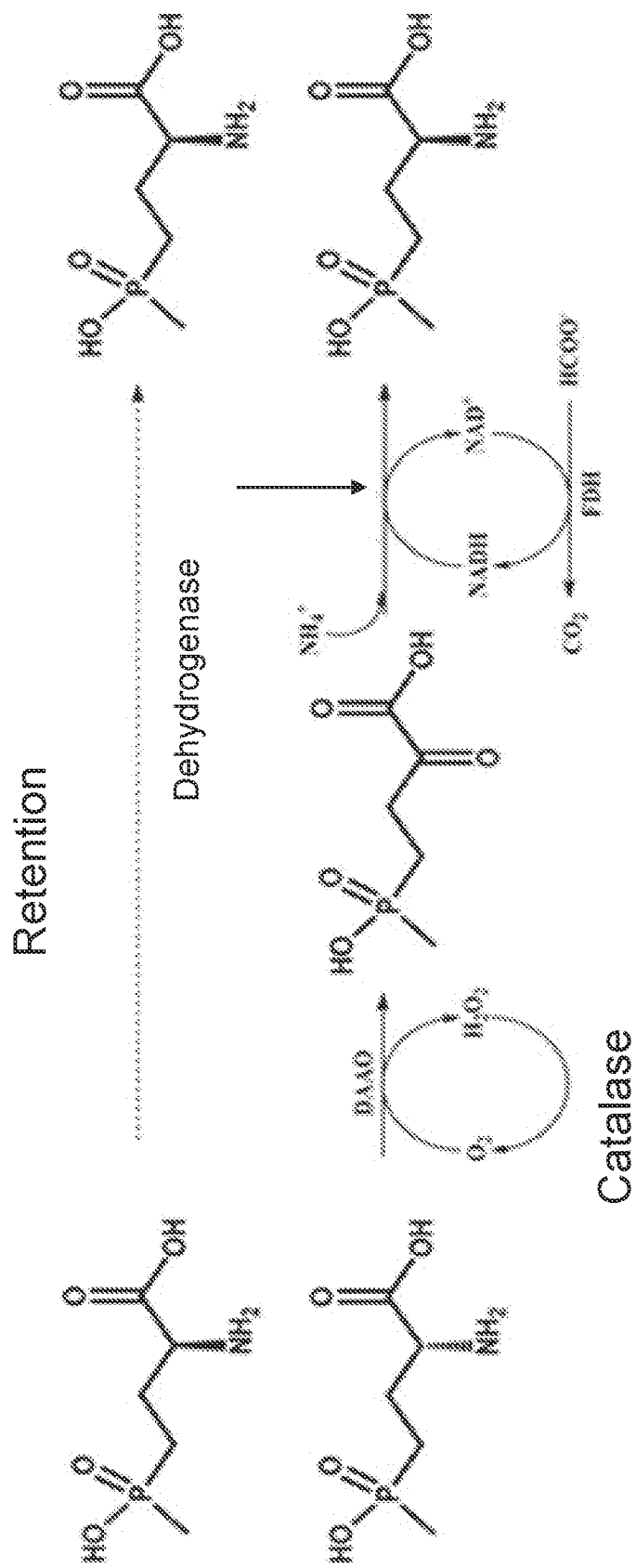
FIG. 3 illustrates an exemplary reaction formula for preparing the L-glufosinate by deracemization (with a formate dehydrogenase coenzyme recycling system) according to some embodiments of the present disclosure.

FIG. 1 illustrates an exemplary reaction formula for preparing the L-glufosinate by a multi-enzyme system resolution manner according to some embodiments of the present disclosure, wherein the obtained L-glufosinate is prepared by deracemization in the presence of the enzymatic system (containing the alcohol dehydrogenase coenzyme recycling system). FIG. 2 illustrates an exemplary reaction formula for preparing the L-glufosinate by deracemization in the presence of the enzymatic system (with the glucose dehydrogenase coenzyme recycling system). FIG. 3 illustrates an exemplary reaction formula for preparing the L-glufosinate in the presence of the enzymatic system (with the formate dehydrogenase coenzyme recycling system).

The formate dehydrogenase (FDH) described in the embodiments of the present disclosure may be any enzyme or enzyme variant having a formate dehydrogenase activity known in the art. In some embodiments, the formate dehydrogenase may be derived from *LactoBacillus buchneri*. In some embodiments, an amino acid sequence of the formate dehydrogenase may have at least 90%, 91%, 92%, 93%, 94%, 95%, 96%, 97%, 98%, or 99% identity to SEQ ID No. 2. In some embodiments, a nucleotide sequence of the formate dehydrogenase may have at least 90%, 91%, 92%, 93%, 94%, 95%, 96%, 97%, 98%, or 99% identity to SEQ ID No. 7.

The glucose dehydrogenase (GDH) described in the embodiments of the present disclosure may be any enzyme or enzyme variant having a glucose dehydrogenase activity known in the art. In some embodiments, the glucose dehydrogenase may be derived from *Exiguobacterium sibiricum*. In some embodiments, an amino acid sequence of the glucose dehydrogenase may have at least 90%, 91%, 92%, 93%, 94%, 95%, 96%, 97%, 98%, or 99% identity to SEQ ID NO. 3. In some embodiments, a nucleotide sequence of the glucose dehydrogenase may have at least 90%, 91%, 92%, 93%, 94%, 95%, 96%, 97%, 98%, or 99% identity to SEQ ID NO. 8.

The alcohol dehydrogenase (ADH) described in the embodiments of the present disclosure may be any enzyme or enzyme variant having an alcohol dehydrogenase activity known in the art. In some embodiments, the alcohol dehydrogenase may be derived from *LactoBacillus brevis*. In some embodiments, an amino acid sequence of the alcohol dehydrogenase may have at least 90%, 91%, 92%, 93%, 94%, 95%, 96%, 97%, 98%, or 99% identity to SEQ ID NO.

4. In some embodiments, a nucleotide sequence of the alcohol dehydrogenase may have at least 90%, 91%, 92%, 93%, 94%, 95%, 96%, 97%, 98%, or 99% identity to SEQ ID NO. 9.

The enzymes (e.g., the D-amino acid oxidase mutant, the Glu/Leu/Phe/Val dehydrogenase, the catalase, the formate dehydrogenase, the glucose dehydrogenases, or the alcohol dehydrogenase) described in embodiments of the present disclosure may be in the form of a purified enzyme, a partially purified enzyme, a cell-free extract or crude cellular extract, a liquid, powders, or immobilized forms, permeabilized cells containing enzymes, intact cells, or an intact fermentation broth or any other suitable form. In some embodiments, each enzyme in the enzymatic system may be obtained independently from a free enzyme and a recombinant host cell expressing the enzyme.

In some embodiments, the recombinant host cell may be selected from *Saccharomyces, Aspergillus, Pichia, Kluyveromyces, Candida, Hansenula, Humicola, Issatchenkia, Trichosporon, Brettanomyces, Pachysolen, Yarrowia, Actinomycetes, Streptomyces, Bacillus* or *Escherichia*. For example, the recombinant host cell may be selected from *Saccharomyces cerevisiae, Yarrowia lipolitica, Candida krusei, Issatchenkia orientalis, Bacillus subtilis* or *Escherichia coli*.

In some embodiments, a conversion reaction may be carried out in a reaction solution, and the reaction solution may have a pH of 7-10. A high reaction efficiency can be obtained when the conversion reaction is carried out in the reaction solution having a pH of 7-10. In preferred embodiments, the reaction solution may have a pH of 8-9.

The method described in embodiments of the present disclosure may comprise: step a) performing an oxidation reaction catalyzed by the D-amino acid oxidase mutant; and step b) performing a transamination reaction catalyzed by the Glu/Leu/Phe/Val dehydrogenase.

In some embodiments, a temperature of the oxidation reaction in the step a) may be in a range of 25° C.-45° C. For example, the temperature of the oxidation reaction may be 30° C., 35° C., 40° C., or 45° C., etc., or a range between any two values.

In some embodiments, a time of the oxidation reaction in the step a) may be in a range of 6-24 h. For example, the time of the oxidation reaction may be 6 h, 8 h, 10 h, 12 h, 14 h, 16 h, 18 h, 20 h, or 24 h, etc., or a range between any two values.

In some embodiments, in the step b), the PPO produced in the step a) may be catalytically reduced to the L-glufosinate by the L-amino acid dehydrogenase, thereby realizing in situ deracemization of the D, L-glufosinate to obtain the L-glufosinate with an enantiomeric excess greater than 99%.

In some embodiments, a reaction system in the step b) may further comprise a coenzyme NADH. In some embodiments, a molar ratio of the NADH to a substrate may be in a range of 1:5000-1:10. For example, the molar ratio of the NADH to the substrate may be 1:10, 1:100, 1:500, 1:1000, 1:2000, 1:3000, 1:4000, or 1:5000, or the like. In some embodiments, an addition of the NADH may be 0.1-2 mM (molar concentration). More preferably, the addition of the NADH may be 0.5 mM.

In some embodiments, a temperature of a reductive amination reaction in the step b) may be in a range of 25° C.-45° C. For example, the temperature of the reductive amination reaction may be 20° C., 25° C., 30° C., 35° C., 40° C., or 45° C., etc., or a range between any two values.

In some embodiments, a time of the reductive amination reaction in the step b) may be in a range of 6-24 h. For example, the time of the reductive amination reaction may be 6 hours, 8 h, 10 h, 12 h, 14 h, 16 h, 18 h, 20 h, or 24 h, etc., or a range between any two values.

In some embodiments, in the step b), a molar ratio of an inorganic ammonium donor to the substrate may be in a range of 1:1-10:1 when the reaction starts. For example, the molar ratio of the inorganic ammonium donor to the substrate may be 1:1, 3:1, 5:1, 7:1, or 9:1, or the like.

In some embodiments, in the step b), the inorganic ammonium donor may be ammonium phosphate, ammonium chloride, ammonium sulfate, ammonium formate, ammonium acetate, or ammonia. Preferably, the inorganic ammonium donor may be the ammonium phosphate, ammonium formate, or ammonia. More preferably, the inorganic ammonium donor may be the ammonia.

In some embodiments, no additional hydrogen peroxide may be added for the method of embodiments of the present disclosure. The D-amino acid oxidase or mutant thereof in this method utilizes oxygen efficiently in a catalytic reaction, which can realize the need of efficient catalytic oxidation only at an oxygen concentration supplied through an aeration and stirring process.

The method described in the embodiments of the present disclosure may be carried out in one or more reaction vessels. Preferably, the method described in the embodiments of the present disclosure may be carried out in a reaction vessel (i.e., a "one-pot two-step manner").

In preferred embodiments, the D-amino acid oxidase mutant used in the step a) may be expressed by a first recombinant microorganism. Accordingly, step a) may comprise: obtaining the 4-(Methylhydroxyphosphinyl)-2-oxobutyric acid by oxidizing the D, L-glufosinate in the presence of the first recombinant microorganism and oxygen. The method of embodiments of the present disclosure has higher catalytic efficiency by utilizing the first recombinant microorganism.

Any manner known in the art may be utilized to construct the first recombinant microorganism. For example, the first recombinant microorganism may be constructed as follows: constructing a recombinant expression vector comprising D-amino acid oxidase mutant genes, transforming the recombinant expression vector into a microorganism, performing induced cultivation on the obtained recombinant microorganism, and isolating a culture fluid to obtain a first recombinant microorganism comprising the D-amino acid oxidase mutant genes. Preferably, an addition of the recombinant microorganism may be 1-200 g/L in a reaction solution by weight of wet cells after centrifugation at 10000 rpm for 10 min. More preferably, the addition of the first recombinant microorganism may be 10 g/L-100 g/L in the reaction solution. More preferably, the addition of the first recombinant microorganism may be 30 g/L in the reaction solution.

In some embodiments, the Glu/Leu/Phe/Val dehydrogenase used in the step b) and the enzyme used for the coenzyme recycling may be co-expressed by a second recombinant microorganism. Accordingly, step b) may comprise: obtaining the L-glufosinate by performing reductive amination on the obtained 4-(Methylhydroxyphosphinyl)-2-oxobutyric acid in the step a) in the presence of the second recombinant microorganism for co-expressing Glu/Leu/Phe/Val dehydrogenase and enzymes for coenzyme recycling (e.g., the formic dehydrogenase, the glucose dehydrogenase, or the alcohol dehydrogenase) and inorganic ammonium salts. The method of embodiments of the present disclosure has higher catalytic efficiency by utilizing the second recombinant microorganism.

Any manner known in the art may be utilized to construct the second recombinant microorganism. For example, the second recombinant microorganism may be constructed as follows: constructing a recombinant expression vector comprising the genes of the Glu/Leu/Phe/Val dehydrogenase and enzymes genes for coenzyme recycling, transforming the recombinant expression vector into a microorganism, performing induced cultivation on the obtained microorganism, and isolating a culture fluid to obtain the second recombinant microorganism comprising the genes of the Glu/Leu/Phe/Val dehydrogenase and enzymes for the coenzyme recycling. Preferably, an addition of the second recombinant microorganism may be 1 g/L-200 g/L in a reaction solution by weight of wet cells after centrifugation at 10000 rpm for 10 min. More preferably, the addition of the second recombinant microorganism may be 3 g/L-100 g/L in the reaction solution. More preferably, the addition of the second recombinant microorganism may be 30 g/L in the reaction solution.

In some embodiments, the first and second recombinant microorganisms may be any engineered bacteria suitable for an enzyme expression. In some embodiments, the first and second recombinant microorganisms may be derived from Saccharomyces, Aspergillus, Pichia, Kluyveromyces, Candida, Hansenula, Humicola, Issatchenkia, Trichosporon, Brettanomyces, Pachysolen, Yarrowia, Actinomycetes, Streptomyces, Bacillus or Escherichia. In preferred embodiments, the first and second recombinant microorganisms may be selected from Saccharomyces cerevisiae, Yarrowia lipolitica, Candida krusei, Issatchenkia orientalis, Bacillus subtilis, or Escherichia coli. In more preferred embodiments, the first and second recombinant microorganisms may be both the Escherichia coli.

A yield of the method of the embodiments of the present disclosure may be measured by any manner known in the art. For example, a content of two conformations in the obtained glufosinate may be measured by chiral High-performance liquid chromatography (HPLC). In some embodiments, the enantiomeric excess (e.e.) of the obtained L-glufosinate may have at least 99.0%, 99.5%, or 99.9%. In some embodiments, a yield of the obtained L-glufosinate may be at least 95%, 96%, or 97%.

The capital letters in the present disclosure represent amino acids as known to a person skilled in the art.

The experimental manners in the present disclosure are routine manners if not otherwise stated, and the gene cloning operation may be specifically referred to the "Guide to Molecular Cloning Experiments" edited by J. Sambrook et al.

Description of a Sequence Table

SEQ ID NO.1 is an amino acid sequence annotated as a D-amino acid oxidase (DAAO) derived from *Microbotryum intermedium*.

SEQ ID NO.2 is an amino acid sequence annotated as a formate dehydrogenase (FDH) derived from *LactoBacillus buchneri*.

SEQ ID NO.3 is an amino acid sequence annotated as a glucose dehydrogenase (GDH) derived from *Exiguobacterium sibiricum*.

SEQ ID NO.4 is an amino acid sequence annotated as an alcohol dehydrogenase (ADH) derived from *LactoBacillus brevis*.

SEQ ID NO.5 is an amino acid sequence annotated as a Glu/Leu/Phe/Val dehydrogenase derived from *Delftia acidovorans*.

SEQ ID NO.6 is a nucleotide sequence annotated the D-amino acid oxidase (DAAO) derived from *Microbotryum intermedium*.

SEQ ID NO.7 is a nucleotide sequence annotated as the formate dehydrogenase (FDH) derived from *LactoBacillus buchneri*.

SEQ ID NO. 8 is a nucleotide sequence annotated as the glucose dehydrogenase (GDH) derived from *Exiguobacterium sibiricum*.

SEQ ID NO.9 is a nucleotide sequence annotated as the alcohol dehydrogenase (ADH) derived from *LactoBacillus brevis*.

SEQ ID NO.10 is a nucleotide sequence annotated as the Glu/Leu/Phe/Val dehydrogenase derived from *Delftia acidovorans*.

The D-amino acid oxidase mutant of the embodiments of the present disclosure enables a reaction system to have good catalytic efficiency. Furthermore, when using the racemic D, L-glufosinate as the substrate for a catalytic reaction, it has a conversion rate much higher than the wild-type enzyme and a PPO yield is substantially increased.

EMBODIMENTS

Materials and Methods

Reagents used for upstream genetic engineering include: genome extraction kit, plasmid extraction kit, and DNA purification and recovery kit used in the embodiments purchased from Corning Life Sciences (Wujiang) Co. Ltd; One Step Cloning Kit purchased from Vazyme Co. Ltd.; *E. coli* BL21 (DE3), plasmid pET-28a(+), etc. purchased from Shanghai Xuguan Bio-technology Development Co. Ltd.; DNA labeling, low molecular weight standard protein, protein precast gel purchased from Beijing GenStar Co., Ltd.; ClonExpress II One Step Cloning Kit purchased from Nanjing Vazyme Biotechnology Co., Ltd; pfu DNA polymerase and Dpn I endonuclease purchased from Thermo Fisher Scientific (China) Co., Ltd.; the primer synthesis and sequencing performed by Hangzhou Qingke Zixi Biotechnology Co., Ltd., and the total gene synthesis performed by Sango Biotechnology (Shanghai) Co., Ltd. The use of the above reagents refers to the product manual.

Reagents used in a downstream catalytic process include: 4-(Methylhydroxyphosphinyl)-2-oxobutyric acid (PPO) obtained from Yongnong Bioscience Co., Ltd.; D,L-glufosinate (or D,L-phosphinothricin, D,L-PPT) obtained from Yongnong Bioscience Co., Ltd.; and the other commonly used reagents purchased from Sinopharm Chemical Reagent Co., Ltd.

The reaction is detected and the PPO is analyzed by high-performance liquid chromatography (HPLC) in the embodiments. In the HPLC analysis, a chromatographic column is PBR, a column temperature is 30° C., a flow rate is 1 mL/min, a detection wavelength is 210 nm, and a mobile phase is 5 mM of $(NH_4)_2HPO_4$.

The content of the two conformations of PPT is detected by chiral HPLC analysis. In the chiral HPLC analysis, a chromatographic column is OA-5000L, a mobile phase is 0.5 g/L ammonium cupric sulfate pentahydrate solution, an addition is 0.3% (v/v) acetonitrile, a detection wavelength is 254 nm, a flow rate is 1 mL/min, and a column temperature is 35° C.

Embodiment 1: Construction of a Genetically Engineered Bacteria

After gene synthesis of a gene sequence of a D-amino acid oxidase (DAAO, GenBank number FMSP01000004.1, with an amino acid sequence as set forth in SEQ ID NO.1 and a nucleotide sequence as set forth in SEQ ID NO.6) derived from *Microbotryum intermedium*, pET-28a-daao was obtained by inserting an expression plasmid pET-28a (+). After sequencing verification, the pET-28a-daao was transfected into *E. coli* BL21 (DE3) of an expression host for subsequent expression of a recombinant enzyme.

After gene synthesis of a gene sequence of a formate dehydrogenase (FDH) derived from *LactoBacillus buchneri* (with an amino acid sequence as set forth in SEQ ID NO. 2 and a nucleotide sequence as set forth in SEQ ID NO. 7), pET-28a-fdh was obtained by inserting the expression plasmid pET-28a (+). After sequencing verification, the pET-28a-fdh was transfected into *E. coli* BL21 (DE3) of the expression host for subsequent expression of the recombinant enzyme.

After gene synthesis of a gene sequence of a glucose dehydrogenase (GDH) derived from *Exiguobacterium sibiricum* (with an amino acid sequence set forth in SEQ ID NO. 3 and a nucleotide sequence as set forth in SEQ ID NO. 8), pET-28a-gdh was obtained by inserting the expression plasmid pET-28a (+). After sequencing verification, the pET-28a-gdh was transfected into *E. coli* BL21 (DE3) of the expression host for subsequent expression of the recombinant enzyme.

After gene synthesis of a gene sequence of an alcohol dehydrogenase (ADH) derived from *LactoBacillus brevis* (with an amino acid sequence as set forth in SEQ ID NO. 4 and a nucleotide sequence as set forth in SEQ ID NO. 9), pET-28a-adh was obtained by inserting the expression plasmid pET-28a (+). After sequencing verification, the pET-28a-adh was transfected into *E. coli* BL21 (DE3) of the expression host for subsequent expression of the recombinant enzyme.

After gene synthesis of a gene sequence of a L-amino acid dehydrogenase (LAADH, GenBank number WP_012202150.1, NCBI annotated as a Glu/Leu/Phe/Val dehydrogenase, with an amino acid sequence as set forth in SEQ ID NO. 5 and a nucleotide sequence as forth in SEQ ID NO. 10) derived from *Delftia acidovorans*, a plasmid pET-28a-laadh was obtained by inserting the expression plasmid pET-28a (+). After sequencing verification, the pET-28a-laadh was transferred into *E. coli* BL21 (DE3) of the expression host for subsequent expression of the recombinant enzyme.

Embodiment 2: Cultivation of Engineered Bacterial Cells

After activating engineered bacteria recombinant *E. coli* (*E. coli* BL21(DE3)/pET-28a-DAAO, *E. coli* BL21(DE3)/pET-28a-LAADH, *E. coli* BL21(DE3)/pET-28a-FDH, *E. coli* BL21(DE3)/pET-28a-GDH, and *E. coli* BL21(DE3)/pET-28a-ADH) by plate streaking respectively, single colonies were picked and inoculated into 10 mL of LB liquid medium containing 50 μg/mL kanamycin, and a seed solution was obtained by shaking incubation for 10 h at 37° C. Then the seed solution was transferred to 50 mL of LB liquid medium containing 50 g/mL kanamycin at 2% of inoculum amount, after shaking incubation at 37° C. until the OD600 reached about 0.8, then IPTG at a final concentration of 0.1 mM was added into the LB liquid medium and shaking incubation was continued at 25° C. for 12 h. At the end of cultivation, a culture solution was centrifuged at 8000 rpm for 10 min, a supernatant was discarded, and cells were collected and stored in a ultra-low-temperature refrigerator of −80° C. for later use.

Embodiment 3: Construction of Mutant (at Positions 62 and 226) of the D-Amino Acid Oxidase (DAAO)

Mutations at position 62 and/or position 226 (specifically as represented by F62K and/or M226T) were found on the basis of a wild-type DAAO sequence described in Embodiment 1. Primer sequences for PCR mutations were designed for mutation sites (position 62 and position 226 of the mutated D-amino acid oxidase sequence) as shown in Table 1.

TABLE 1

Primer sequence list

| No. | Primer Name | Primer Sequences | Sequence No. |
|---|---|---|---|
| 1 | F62KF | gattctt gcgggtc caccttg gggcacc agttcgc tc | SEQ ID NO. 11 |
| 2 | F62KR | gagcgaa ctggtgc cccaagg tggaccc gcaagaa tc | SEQ ID NO. 12 |
| 3 | M226TF | ggggtct gacgcat cggtagt gcacagc ttgac | SEQ ID NO. 13 |
| 4 | M226TR | gtcaagc tgtgcac taccgat gcgtcag acccc | SEQ ID NO. 14 |

PCR (25 μL) amplification system was as follows.

The PCR amplification system included 12.5 μL of Pfu buffer, 2 μL of primer, 1 μL of template plasmid, 0.5 μL of dNTP, 1 μL of Pfu, and adding ddH$_2$O to make up to 25 μL.

PCR amplification conditions were as follows.

The PCR amplification conditions included (1) pre-denaturation at 95° C. for 3 min, (2) denaturation at 95° C. for 30 s, (3) annealing at 65° C. for 30 s, (4) extension at 72° C. for 5 min for 20 cycles, (5) extension at 72° C. for 10 min, and (6) storage at 4° C.

After PCR, 5 μL of an amplification product was taken for nucleic acid gel electrophoresis analysis, and a clear target band was obtained. Dpn I endonuclease with a volume of 0.5 μL was added to a remaining amplification product for reaction at 37° C. for 3 h, and a template DNA was digested and a mutant plasmid was retained.

After the reaction, the obtained mutant plasmids (pET-28a-DAAO F62K, pET-28a-DAAO M226T, and pET-28a-DAAO F62K-M226T) were transformed into BL21(DE3) competent cells, and the transformed cells were coated on LB solid medium containing 50 g/mL kanamycin and cultured at 37° C. overnight. Single colonies were picked to obtain mutant transformants. Cells were obtained as described in Embodiment 2 (strain E. coli BL21(DE3)/pET-28a-DAAO F62K, strain E. coli BL21(DE3)/pET-28a-DAAO M226T, and strain E. coli BL21(DE3)/pET-28a-DAAO F62K-M226T respectively).

Embodiment 4: Comparison of Enzyme Activity of the D-Amino Acid Oxidase Mutant The catalytic efficiency of the D-amino acid oxidase was compared with the D-amino acid oxidase mutant by measuring a production of PPO. When only the D-amino acid oxidase and the D-amino acid oxidase mutant were available, an oxidation reaction of D, L-PPT was catalyzed to generate PPO, and a reaction system included: 300 mM racemic glufosinate ammonium salt, 100 mM phosphate buffer with pH 8.0, 8000 U/L catalase, and 20 g/L D-amino acid oxidase or lyophilized cells of its mutant. After reaction for 16 h, a sample reaction solution was taken and processed, a concentration of PPO was determined using HPLC and a conversion rate of PPO was calculated (the conversion rate of PPO=the concentration of PPO/concentration of substrate D-PPT×100%), as shown in Table 2.

TABLE 2

Calculation table of conversion rate

| Enzyme No. | Wild-type/Mutant | remaining D-PPT/mM | PPO/mM | Conversion rate (round to 3 decimal places) |
| --- | --- | --- | --- | --- |
| 1 | Wild-type | 100 ± 11 | 47 ± 5 | 31.3% |
| 2 | F62K | 54 ± 6 | 93 ± 2 | 62.0% |
| 3 | M226T | 34 ± 2 | 121 ± 6 | 80.6% |
| 4 | F62K + M226T | 0 | 147 ± 8 | 98.0% |

As seen from Table 2, conversion rates of the obtained mutant were all higher than conversion rates of the wild-type DAAO. The DAAO mutant 4 has the highest conversion rate of PPO, of which phenylalanine at the position 62 is substituted with lysine, and methionine at the position 226 is substituted with threonine and; in other words, F at the position 62 of the DAAO mutant 4 is substituted with K, and M at the position 226 of the DAAO mutant 4 is substituted with T.

Embodiment 5: Construction of Glu/Leu/Phe/Val Dehydrogenase Mutant (at Positions 91 and 168)

Mutations at the positions 91 and 168 (specifically represented by V91I and N168G) were found on the basis of the wild-type LAADH sequence as described in Embodiment 1. Primer sequences for PCR mutations were designed for mutation sites (positions 91 and 168 of a mutated LAADH sequence) as shown in Table 3.

TABLE 3

Primer sequence list

| No. | Primer Name | Primer Sequences | Sequence No. |
| --- | --- | --- | --- |
| 1 | V91IF | cctggtg gaaacgg atgccgc ccttgcc g | SEQ ID NO. 15 |
| 2 | V91IR | cggcaag ggcggca tccgttt ccaccag g | SEQ ID NO. 16 |
| 3 | N168GF | gggtccg aagaatc ggtcgtg cagcgct tgc | SEQ ID NO. 17 |
| 4 | N168GR | gcaagcg ctgcacg accgatt cttcgga ccc | SEQ ID NO. 18 |

PCR amplification system and PCR amplification conditions were the same as these described in Embodiment 3.

After the reaction, the obtained mutant plasmid (pET-28a-LAADH V91I-N168G) was transformed into BL21(DE3) competent cells, and the transformed cells were coated on LB solid medium containing 50 μg/mL kanamycin and cultured at 37° C. overnight. Single colonies were picked to obtain mutant transformants. Cells were obtained as described in Embodiment 2.

Embodiment 6: Construction of LAADH Expression Strain

I. Construction of an Expression Strain Comprising a Glucose Dehydrogenase Coenzyme Recycling System On the vector pET-28a-LAADH V91I-N168G, a gene fragment of the glucose dehydrogenase was ligated to a polyclonal site by a seamless cloning kit, and an enzyme cleavage site was Hind III, a plasmid pET-28a-LAADH V91I-N168G-GDH was obtained, and an expression strain E. coli BL21(DE3)/pET-28a-LAADH V91I-N168G-GDH was obtained.

II. Construction of an Expression Strain Comprising a Formate Dehydrogenase Coenzyme Recycling System On the vector pET-28a-LAADH V91I-N168G, a gene fragment of the formate dehydrogenase was ligated to the polyclonal site by the seamless cloning kit, and the enzyme cleavage site was Hind III, the plasmid pET-28a-LAADH V91I-N168G-FDH was obtained, and the expression strain E. coli BL21(DE3)/pET-28a-LAADH V91I-N168G-FDH was obtained.

III. Construction of an Expression Strain Comprising an Alcohol Dehydrogenase Coenzyme Recycling System On the vector pET-28a-LAADH V91I-N168G, a gene fragment of the alcohol dehydrogenase was ligated to the polyclonal site by the seamless cloning Kit, and the enzyme cleavage site was Hind III, the plasmid pET-28a-LAADH V91I-N168G-ADH was obtained, and the expression strain E. coli BL21(DE3)/pET-28a-LAADH V91I-N168G-ADH was obtained.

Embodiment 7: Preparation of L-Glufosinate by Deracemization of Double-Bacteria Multi-Enzyme (Comprising a Glucose Dehydrogenase GDH Coenzyme Recycling System)

According to Embodiment 2, the strain E. coli BL21 (DE3)/pET-28a-DAAO F62K-M226T capable of expressing D-amino acid oxidase and the expression strain *E. coli* BL21(DE3)/pET-28a-LAADH V91I-N168G-GDH capable of expressing an L-amino acid dehydrogenase and a glucose dehydrogenase were cultured, and bacterial cells were collected by centrifugation and lyophilized.

In a reactor of 1 L, 600 mL of ammonium phosphate buffer (pH=8.0, 100 mM) was added, which contains 400 mM D, L-PPT, 8000 U/L catalase, 5% (v/v) defoamer, 20 g/L cell of *E. coli* BL21(DE3)/pET-28a-DAAO F62K-M226T, 20 g/L cell of *E. coli* BL21(DE3)/pET-28a-LAADH V91I-N168G-GDH, 0.5 mM NADH, and 250 mM glucose, air was introduced at a rate of 2 L/min, and ammonia was added to control the pH to 8, then the reaction was carried out at a temperature of 30° C. for 24 h. At the end of the reaction, the liquid-phase detection result of the L-PPT was 388 mM, the enantiomeric excess (e.e.) of the L-PPT was greater than 99%, and the conversion rate of the L-PPT was 97%.

Embodiment 8: Preparation of L-Glufosinate by Deracemization of Double-Bacteria Multi-Enzyme (Comprising a Formate Dehydrogenase Coenzyme Recycling System)

According to Embodiment 2, the strain *E. coli* BL21 (DE3)/pET-28a-DAAO F62K-M226T capable of expressing the D-amino acid oxidase and the expression strain *E. coli* BL21(DE3)/pET-28a-LAADH V91I-N168G-FDH capable of expressing the L-amino acid dehydrogenase and the formate dehydrogenase were cultured, bacterial cells were collected by centrifugation and lyophilized.

In a reactor of 1 L, 600 mL of ammonium phosphate buffer (pH=8.0, 100 mM) was added, which contains 400 mM D,L-PPT, 8000 U/L catalase, 5% (v/v) defoamer, 20 g/L *E. coli* BL21(DE3)/pET-28a-DAAO F62K-M226T lyophilized bacteriophage, 20 g/L lyophilized cell of *E. coli* BL21(DE3)/pET-28a-LAADH V91I-N168G-FDH, 0.5 mM NADH and 250 mM ammonium formate, air was introduced at a rate of 2 L/min, ammonia was used to control the pH to 8, and a reaction was carried out at a temperature of 30° C. for 24 h. At the end of the reaction, the liquid phase detection result of the L-PPT was 382 mM, the enantiomeric excess (e.e.) of the L-PPT was greater than 99%, and the conversion rate of the L-PPT was 95.5%.

Embodiment 9: Preparation of L-Glufosinate by Deracemization of Double-Bacteria Multi-Enzyme (Comprising an Alcohol Dehydrogenase Coenzyme Recycling System)

According to Embodiment 2, the strain *E. coli* BL21 (DE3)/pET-28a-DAAO F62K-M226T capable of expressing the D-amino acid oxidase and the expression strain *E. coli* BL21(DE3)/pET-28a-LAADH V91I-N168G-ADH capable of expressing the L-amino acid dehydrogenase and the alcohol dehydrogenase were cultured, and bacterial cells were collected by centrifugation and lyophilized.

Figure 4A:
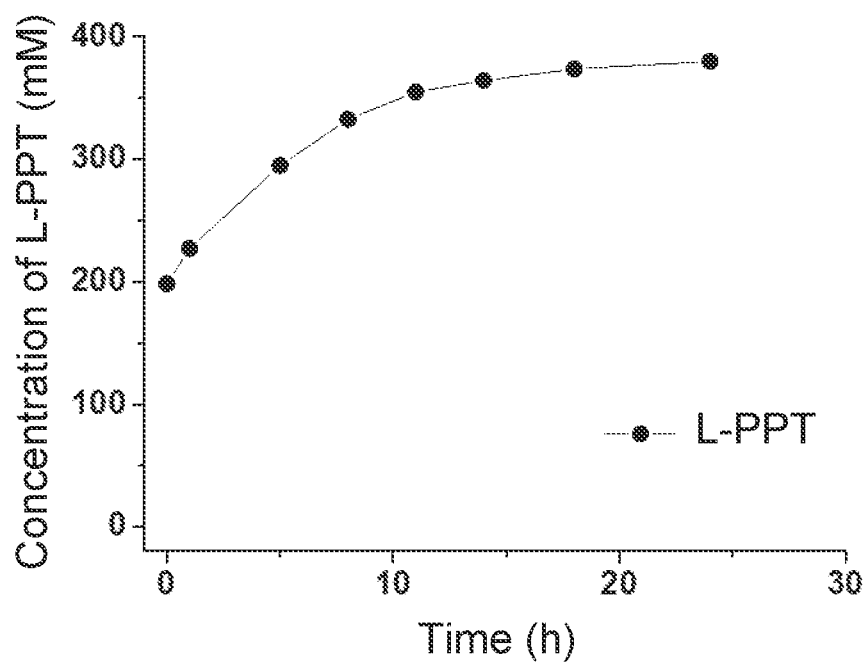
FIG. 4A and FIG. 4B illustrate exemplary reaction processes for preparing the L-glufosinate by deracemization using a double-bacteria multi-enzyme one-pot two-step manner according to some embodiments of the present disclosure.
Figure 4B:
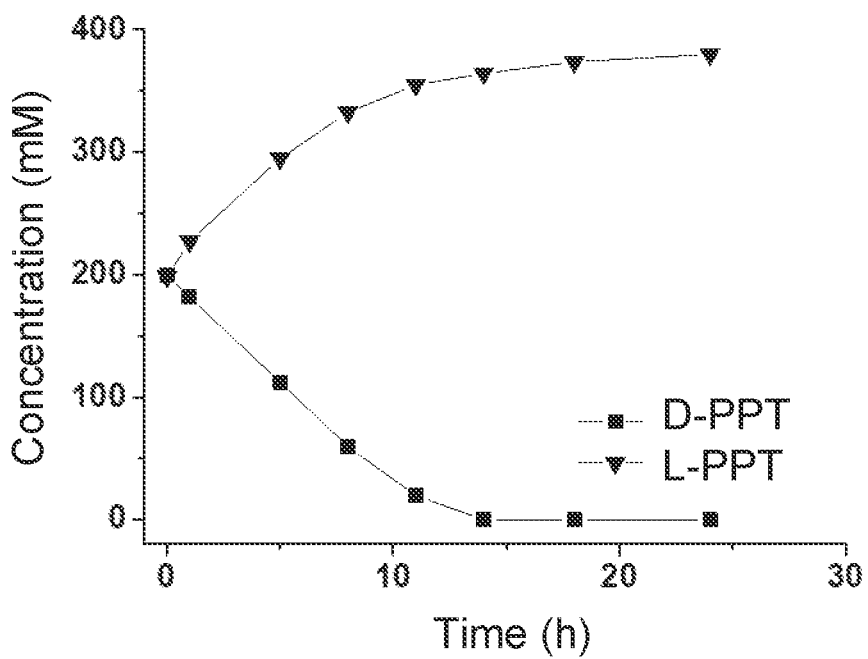

In a reactor of 1 L, 600 mL of reaction solution (pH being adjusted to 8.0 using ammonia) was added, which contains 400 mM D,L-PPT, 8000 U/L catalase, 0.5% (v/v) antifoam, 20 g/L lyophilized cell of *E. coli* BL21(DE3)/pET-28a-DAAO F62K-M226T, 20 g/L lyophilized cell of *E. coli* BL21(DE3)/pET-28a-LAADH V91I-N168G-ADH, 0.5 mM NADH, and 250 mM isopropanol, air was introduced at a rate of 2 L/min, ammonia was used to control the pH to 8, and a reaction was carried out at a temperature of 30° C. for 24 h. The consumption of D-PPT and the generation of L-PPT during the reaction were detected by the liquid phase detection shown in the Embodiments, and reaction process curves are shown in FIGS. 4A and 4B. FIG. 4A and FIG. 4B show that a concentration of the D-PPT gradually decreased and a concentration of the L-PPT gradually increased with time. At the end of the reaction, the liquid phase detection result of the L-PPT was 380 mM, the enantiomeric excess (e.e.) of the L-PPT was greater than 99%, and a conversion rate of the L-PPT was 95%.

Obviously, the foregoing embodiments are merely examples for the sake of clarity and are not a limitation of the embodiments. Other variations or changes in different forms may be made on the basis of the above description for those of ordinary skill in the art. It is not necessary or possible to list all embodiments here. And obvious variations or changes derived therefrom remain within the scope of protection of the present disclosure.

What is claimed is:

1. A D-amino acid oxidase mutant, having an amino acid substitution at least one of position 62 and position 226 of the amino acid sequence of the D-amino acid oxidase mutant when compared to the amino acid sequence of a D-amino acid oxidase as set forth in SEQ ID NO. 1, the position 62 and position 226 being defined with reference to the SEQ ID NO. 1, and the amino acid sequence of the D-amino acid oxidase mutant having at least 90% identity to the SEQ ID NO. 1.

2. The D-amino acid oxidase mutant of claim 1, wherein methionine at the position 226 is substituted with threonine.

3. The D-amino acid oxidase mutant of claim 2, wherein phenylalanine at the position 62 is substituted with lysine.

4. The D-amino acid oxidase mutant of claim 1, wherein the D-amino acid oxidase mutant is derived from *Microbotryum intermedium*.

5. The D-amino acid oxidase mutant of claim 1, wherein the D-amino acid oxidase mutant has an amino acid sequence having at least 99% identity to the SEQ ID NO. 1.

6. A method for preparing L-glufosinate, comprising: generating the L-glufosinate by converting D-glufosinate in the presence of an enzymatic system, wherein the enzymatic system comprises a D-amino acid oxidase mutant for converting the D-glufosinate to 4-(Methylhydroxyphosphinyl)-2-oxobutyric acid; and the D-glufosinate is initially present in a racemic mixture of the D-glufosinate and the L-glufosinate or salts thereof, wherein the D-amino acid oxidase mutant has an amino acid substitution at least one of position 62 and position 226 of the amino acid sequence of the D-amino acid oxidase mutant when compared to the amino acid sequence of a D-amino acid oxidase as set forth in SEQ ID NO. 1, the position 62 and position 226 are defined with reference to the SEQ ID NO. 1, and the amino acid sequence of the D-amino acid oxidase mutant has at least 90% identity to the SEQ ID NO. 1.

7. The method of claim 6, wherein the enzymatic system further comprises an L-amino acid dehydrogenase for converting 4-(Methylhydroxyphosphinyl)-2-oxobutyric acid to the L-glufosinate.

8. The method of claim 6, wherein the enzymatic system further comprises a catalase.

9. The method of claim 6, wherein the enzymatic system further comprises a coenzyme recycling system which is selected from at least one of the following:
   (1) a formate dehydrogenase coenzyme recycling system comprising a formate dehydrogenase, formate and a coenzyme;
   (2) a glucose dehydrogenase coenzyme recycling system comprising a glucose dehydrogenase, glucose and a coenzyme; and
   (3) an alcohol dehydrogenase coenzyme recycling system comprising an alcohol dehydrogenase, isopropanol and a coenzyme.

10. The method of claim 6, wherein each enzyme in the enzymatic system is obtained independently from: a free enzyme and a recombinant host cell expressing the enzyme.

11. The method of claim 10, wherein the recombinant host cell is selected from: *Saccharomyces cerevisiae, Yarrowia lipolitica, Candida krusei, Issatchenkia orientalis, Actinomycetes, Streptomyces, Bacillus subtilis* or *Escherichia coli*.

12. The method of claim 10, wherein a total addition of the recombinant host cell is 1-200 g/L by weight of wet cells in a reaction solution for a conversion reaction.

13. The method of claim 6, wherein a reaction solution for a conversion reaction has a pH of 7-10.

14. The method of claim 13, wherein the reaction solution for the conversion reaction has a pH of 8-9.

15. The method of claim 6, wherein the D-amino acid oxidase mutant catalyzes an oxidation reaction at a reaction temperature of 25° C.-45° C. for 6-24 h.

* * * * *